US011721426B2

United States Patent
Torii

(10) Patent No.: US 11,721,426 B2
(45) Date of Patent: Aug. 8, 2023

(54) ULTRASOUND DIAGNOSTIC APPARATUS, PANORAMIC IMAGE GENERATION METHOD, AND RECORDING MEDIUM

(71) Applicant: Konica Minolta, Inc., Tokyo (JP)

(72) Inventor: Ryota Torii, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 638 days.

(21) Appl. No.: 16/881,608

(22) Filed: May 22, 2020

(65) Prior Publication Data

US 2020/0411165 A1 Dec. 31, 2020

(30) Foreign Application Priority Data

Jun. 25, 2019 (JP) ................................. 2019-116842

(51) Int. Cl.
| | | |
|---|---|---|
| *G16H 30/40* | (2018.01) | |
| *A61B 8/14* | (2006.01) | |
| *A61B 8/08* | (2006.01) | |
| *G16H 30/20* | (2018.01) | |
| *A61B 8/00* | (2006.01) | |
| *G06T 11/60* | (2006.01) | |

(52) U.S. Cl.
CPC ............. *G16H 30/40* (2018.01); *A61B 8/14* (2013.01); *A61B 8/461* (2013.01); *A61B 8/488* (2013.01); *A61B 8/5215* (2013.01); *G06T 11/60* (2013.01); *G16H 30/20* (2018.01)

(58) Field of Classification Search
CPC .......... G16H 30/40; G16H 30/20; A61B 8/14; A61B 8/461; A61B 8/488; A61B 8/5215; A61B 8/469; A61B 8/5207; A61B 8/5238; A61B 8/5246; A61B 8/5276; G06T 11/60; G01S 7/52065
See application file for complete search history.

(56) References Cited

U.S. PATENT DOCUMENTS 5,782,766 A * 7/1998 Weng .................... G06V 10/24
600/443

FOREIGN PATENT DOCUMENTS

| JP | 2003-038487 A | 2/2003 |
| JP | 2015-039521 A | 3/2015 |
| JP | 2015-144623 A | 8/2015 |

OTHER PUBLICATIONS

Office Action/Search Report dated Dec. 13, 2022, for corresponding Japanese Application No. 2019-116842, with English translation.

* cited by examiner

*Primary Examiner* — Bo Joseph Peng
(74) *Attorney, Agent, or Firm* — Lucas & Mercanti, LLP

(57) ABSTRACT

An ultrasound diagnostic apparatus includes: an image generator that generates ultrasound image data based on a reception signal obtained from a moving ultrasound probe; an evaluator that evaluates an index regarding suitability of combining a plurality of pieces of ultrasound image data generated by the image generator and generates an evaluation result; and a combiner that selects ultrasound image data according to the generated evaluation result and combines the ultrasound image data to generate panoramic image data.

17 Claims, 11 Drawing Sheets

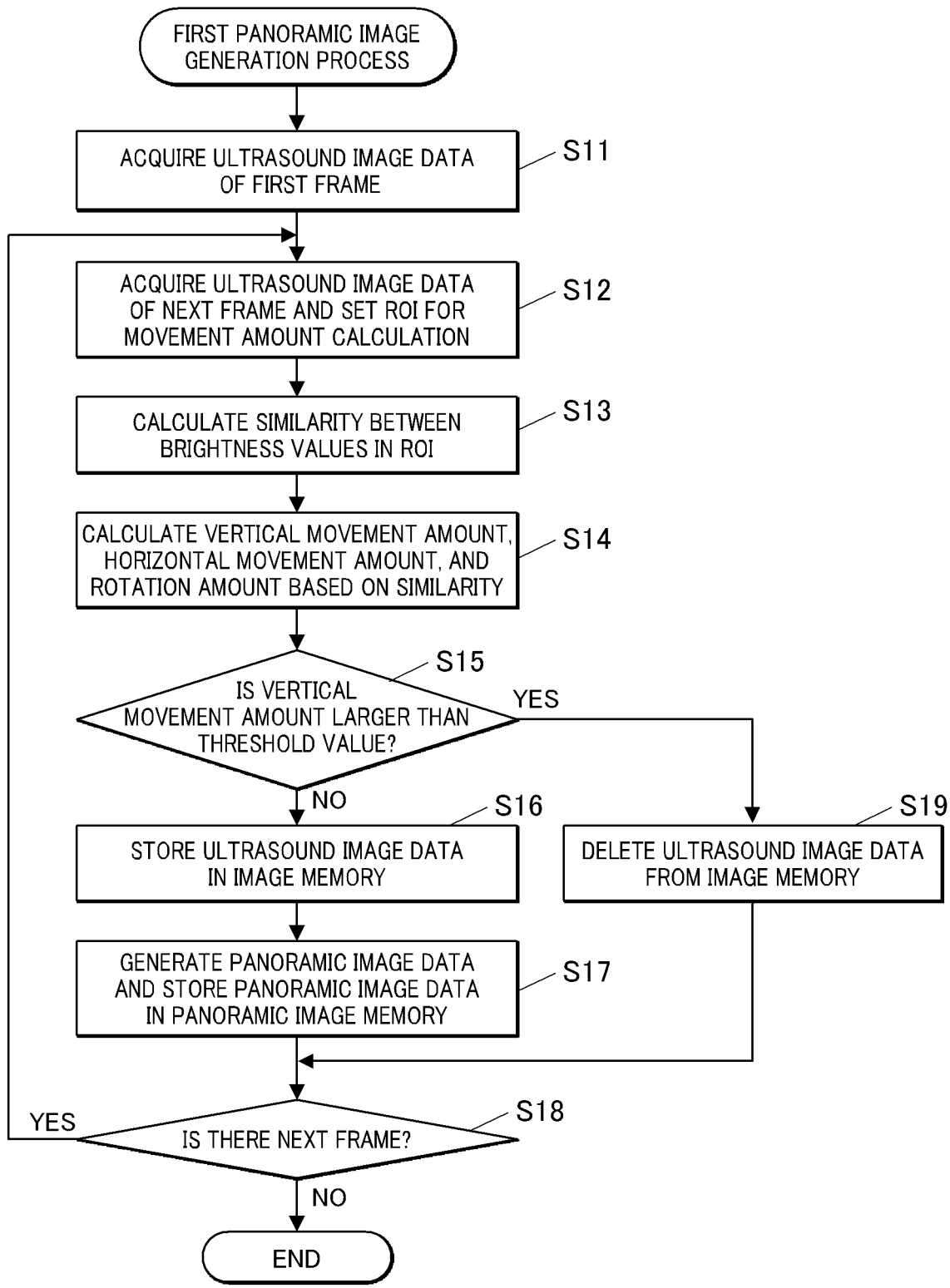

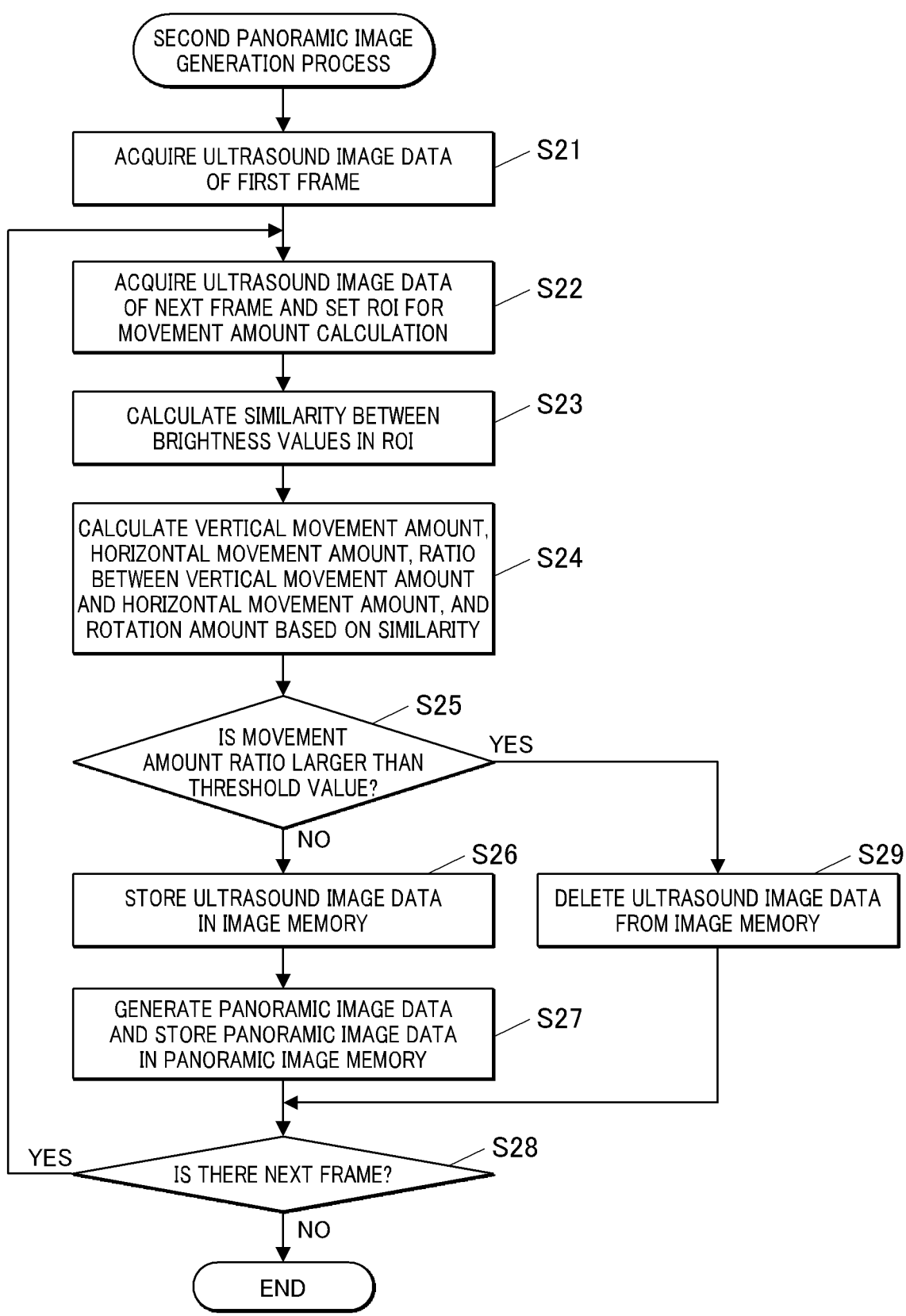

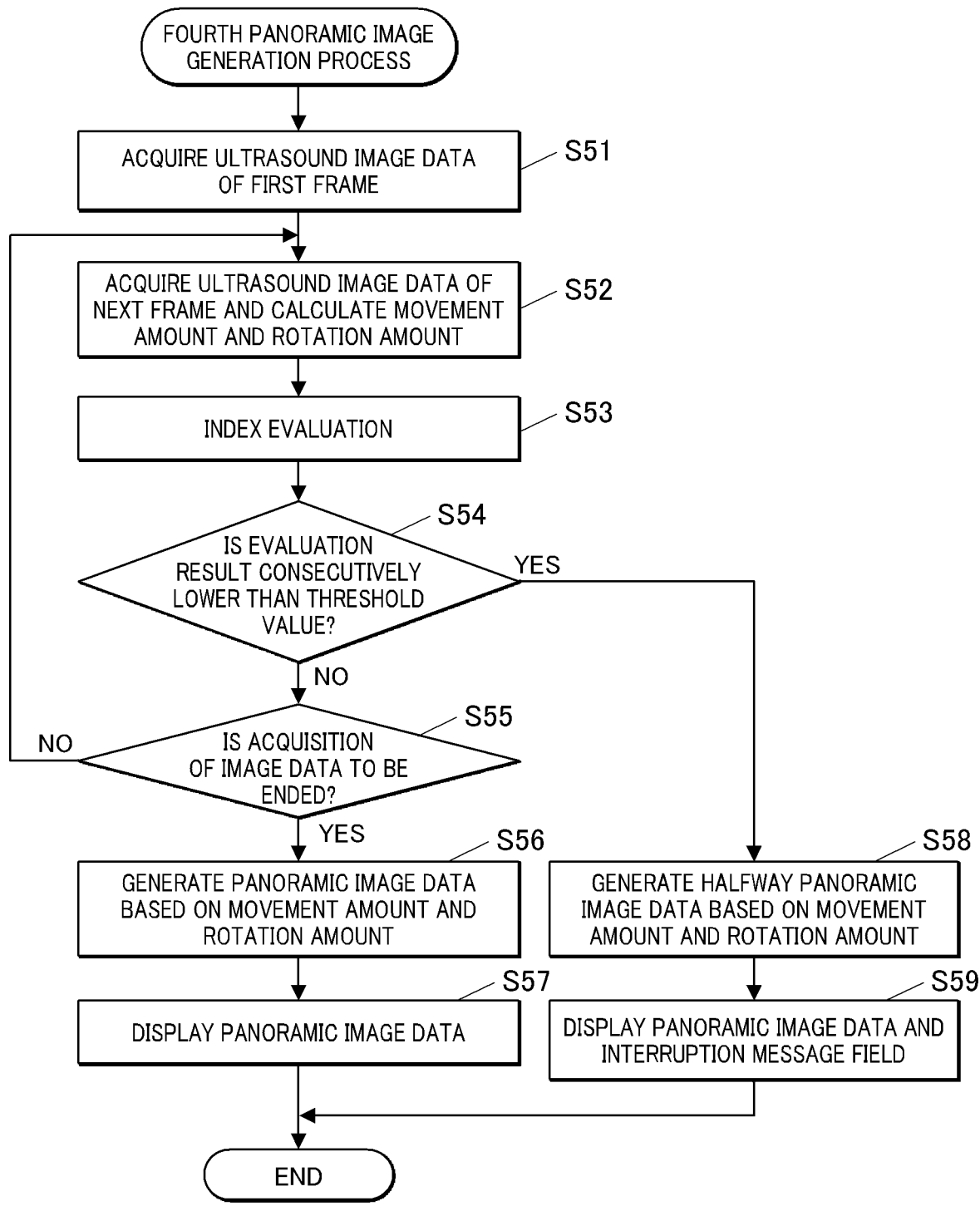

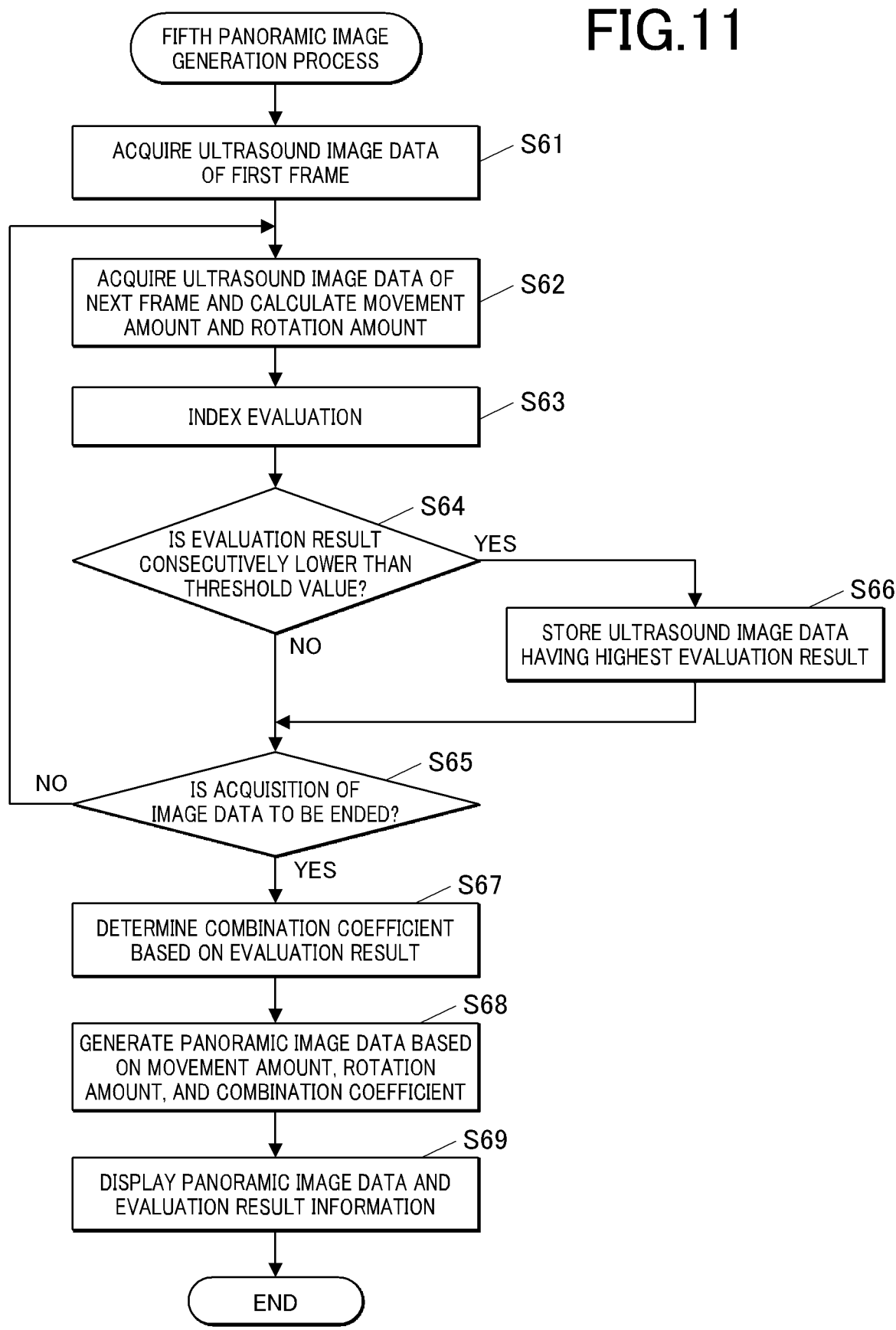

ULTRASOUND DIAGNOSTIC APPARATUS, PANORAMIC IMAGE GENERATION METHOD, AND RECORDING MEDIUM

CROSS-REFERENCE TO RELATED APPLICATIONS

The entire disclosure of Japanese Patent Application No. 2019-116842 filed on Jun. 25, 2019 is incorporated herein by reference in its entirety.

BACKGROUND

Technological Field

The present invention relates to an ultrasound diagnostic apparatus, a panoramic image generation method, and a recording medium.

Description of the Related Art

In ultrasound diagnosis, an examination can be performed repeatedly since the state of the heart or fetus is obtained as an ultrasound image with a simple operation of applying an ultrasound probe to the body surface or the inside of the body cavity of a patient and the safety is high. An ultrasound diagnostic apparatus used to perform such an ultrasound diagnosis is known. Ultrasound image data is obtained by transmitting ultrasound waves from an ultrasound probe having a piezoelectric element to a subject, receiving reflected ultrasound waves by the ultrasound probe, and performing various kinds of processing on the received signal.

There is known an ultrasound diagnostic apparatus having a panoramic image acquisition function for obtaining ultrasound image data (panoramic image data) with a wide field of view by continuously combining a plurality of pieces of ultrasound image data whose positions obtained by moving an ultrasound probe in the opening direction (azimuth direction (lateral direction), scanning direction) are adjacent to each other. However, if the amount of movement of the ultrasound probe in the vertical direction is large, smooth panoramic image data may not be generated due to the difference in the amount of distortion of an observation target. For this reason, there is known an ultrasound diagnostic apparatus that detects a deviation width of a plurality of ultrasound images in the vertical direction and corrects the deviation width to generate panoramic image data (see JP 2003-38487A).

There is also known an ultrasound diagnostic apparatus that evaluates the reliability of a superimposed image (panoramic image data) based on the amount of movement of a plurality of ultrasound images and displays the evaluation result (see JP 2015-144623A).

SUMMARY

The ultrasound diagnostic apparatus disclosed in JP 2003-38487A detects and corrects the deviation width (movement amount) in the vertical (longitudinal) direction. However, distortion or discontinuous portions may occur in a composite image due to the correction by parallel movement, so that panoramic image data that is not useful for diagnosis may be obtained. In the ultrasound diagnostic apparatus disclosed in JP 2015-144623A, the reliability of the superimposed image is evaluated based on the movement amount and presented to the user. However, a composite image in a portion with low reliability may include distortion or the like and accordingly may not be used for diagnosis. In a case where the reliability in the vicinity of a target observation part is low, it is necessary to reacquire an ultrasound image. This causes a problem of wasted time.

It is an object of the present invention to obtain panoramic image data useful for diagnosis. It is another object of the present invention to efficiently obtain panoramic image data useful for diagnosis.

To achieve at least one of the abovementioned objects, according to an aspect of the present invention, an ultrasound diagnostic apparatus reflecting one aspect of the present invention comprises: an image generator that generates ultrasound image data based on a reception signal obtained from a moving ultrasound probe; an evaluator that evaluates an index regarding suitability of combining a plurality of pieces of ultrasound image data generated by the image generator and generates an evaluation result; and a combiner that selects ultrasound image data according to the generated evaluation result and combines the ultrasound image data to generate panoramic image data.

To achieve at least one of the abovementioned objects, according to another aspect of the present invention, a panoramic image generation method reflecting one aspect of the present invention comprises: generating ultrasound image data based on a reception signal obtained from a moving ultrasound probe; evaluating an index regarding suitability of combining a plurality of pieces of ultrasound image data generated in the generating of the ultrasound image data and generating an evaluation result; and selecting ultrasound image data according to the generated evaluation result and combining the ultrasound image data to generate panoramic image data.

To achieve at least one of the abovementioned objects, according to yet another aspect of the present invention, a recording medium reflecting one aspect of the present invention stores a program that causes a computer to perform: generating ultrasound image data based on a reception signal obtained from a moving ultrasound probe; evaluating an index regarding suitability of combining a plurality of pieces of ultrasound image data generated in the generating of the ultrasound image data and generating an evaluation result; and selecting ultrasound image data according to the generated evaluation result and combining the ultrasound image data to generate panoramic image data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein:

FIG. 3 is a flowchart illustrating a first panoramic image generation process;

FIG. 5 is a flowchart illustrating a second panoramic image generation process;

FIG. 9 is a flowchart illustrating a fourth panoramic image generation process;

FIG. 11 is a flowchart illustrating a fifth panoramic image generation process.

DETAILED DESCRIPTION OF THE EMBODIMENTS

An embodiment according to the present invention and first to fourth modification examples will be sequentially described in detail with reference to the accompanying diagrams. However, the scope of the invention is not limited to the disclosed embodiments.

EMBODIMENT

Figure 1:
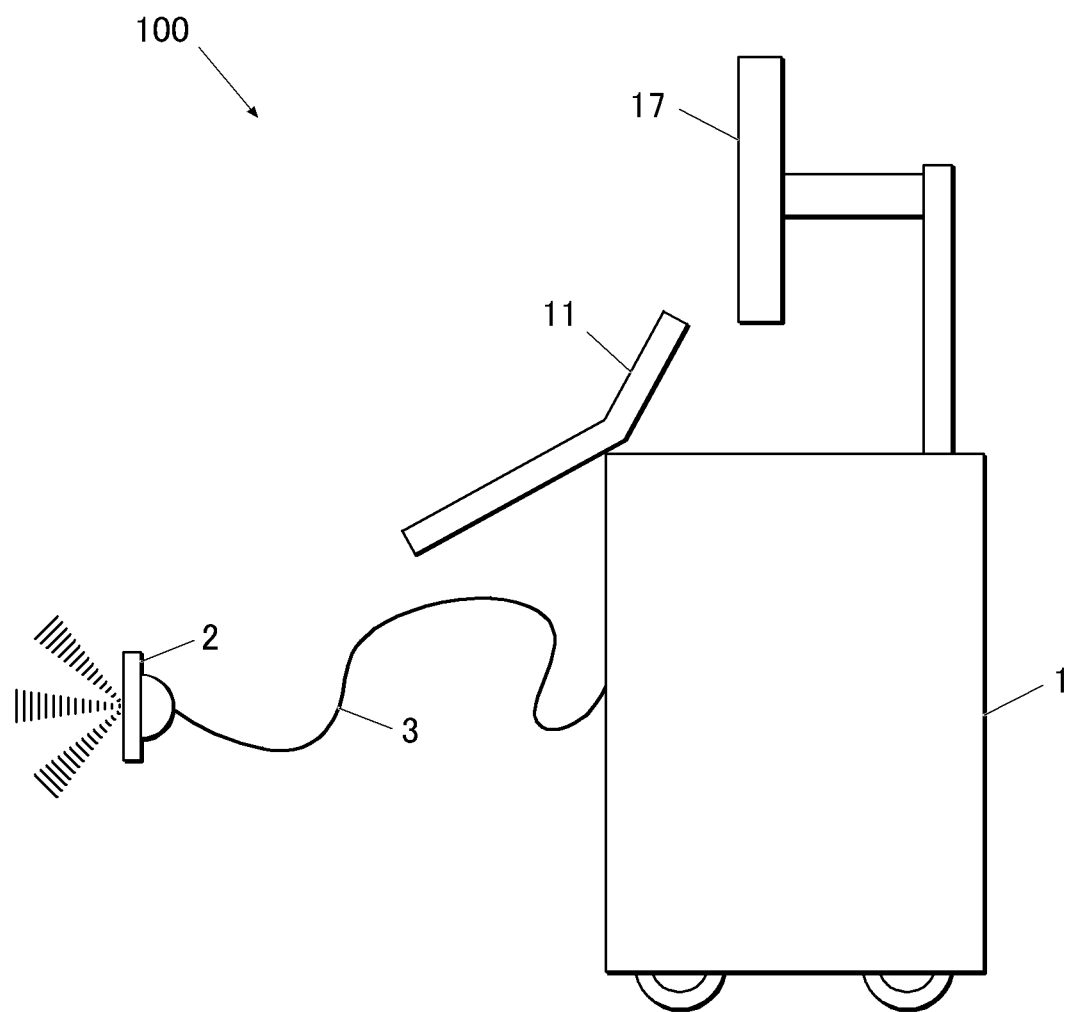
FIG. 1 is an external view of an ultrasound diagnostic apparatus according to an embodiment of the present invention.
Figure 2:
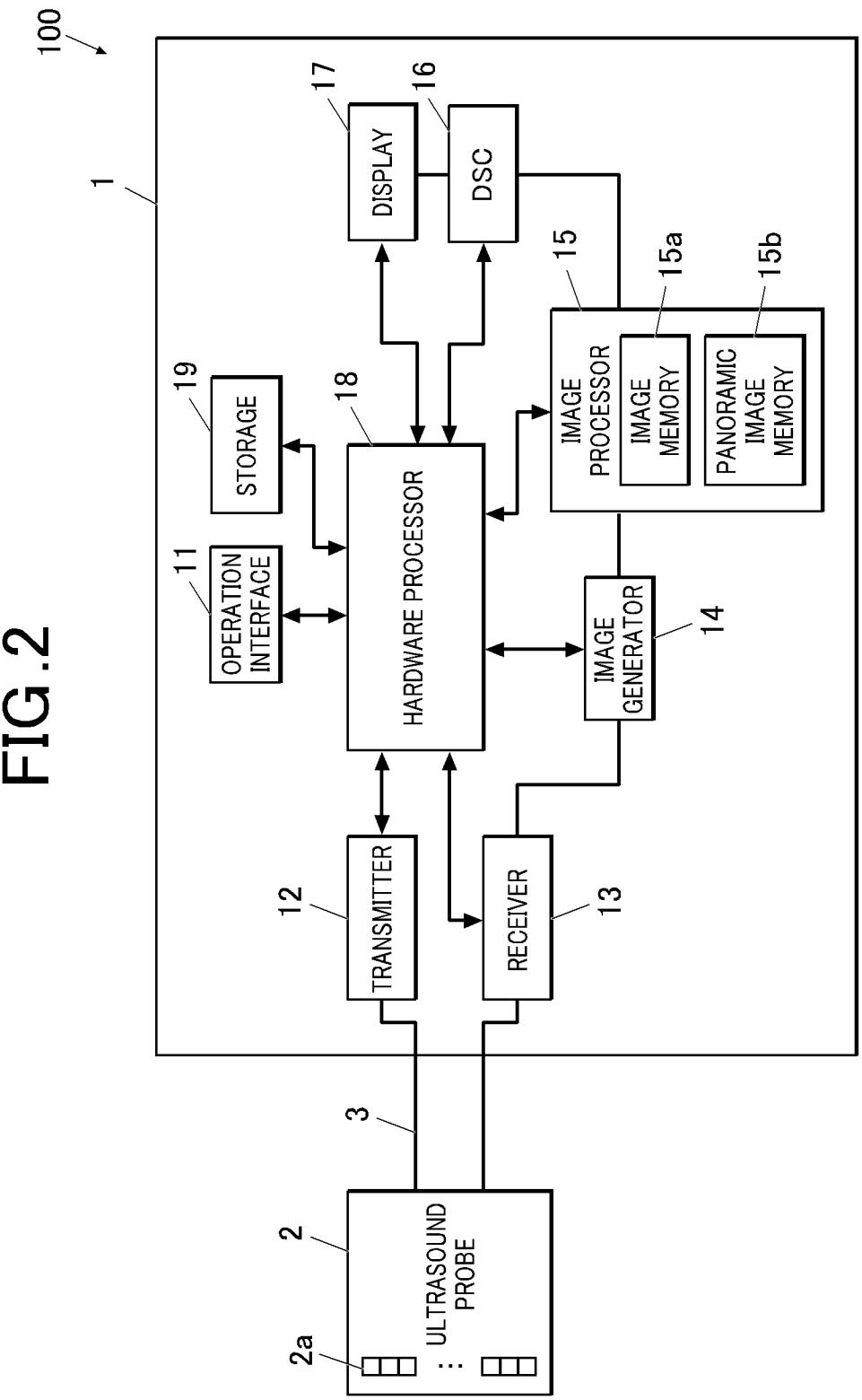
FIG. 2 is a block diagram illustrating the functional configuration of the ultrasound diagnostic apparatus.

An embodiment according to the present invention will be described with reference to FIGS. 1 to 4C. First, the apparatus configuration of the present embodiment will be described with reference to FIGS. 1 and 2. FIG. 1 is an external view of an ultrasound diagnostic apparatus 100 according to the present embodiment. FIG. 2 is a block diagram illustrating the functional configuration of the ultrasound diagnostic apparatus 100.

As illustrated in FIGS. 1 and 2, the ultrasound diagnostic apparatus 100 includes an ultrasound diagnostic apparatus body 1 and an ultrasound probe 2. The ultrasound probe 2 transmits ultrasound waves (transmission ultrasound waves) to a subject, such as a living body of a patient (not illustrated), and receives reflected waves (reflected ultrasound waves: echoes) of the ultrasound waves reflected from the subject. The ultrasound diagnostic apparatus body 1 is connected to the ultrasound probe 2 through a cable 3, and causes the ultrasound probe 2 to transmit transmission ultrasound waves to the subject by transmitting a driving signal as an electrical signal to the ultrasound probe 2, and images the internal state of the subject as an ultrasound image based on a reception signal, which is an electrical signal generated by the ultrasound probe 2 according to the reflected ultrasound waves from the inside of the subject that are received by the ultrasound probe 2.

The ultrasound probe 2 includes transducers (refer to FIG. 2) that are piezoelectric elements, and a plurality of transducers are arranged in a one-dimensional array in the azimuth direction (scanning direction), for example. In the present embodiment, for example, the ultrasound probe 2 including 192 transducers is used. The transducers may be arranged in a two-dimensional array. The number of transducers can be set arbitrarily. In the present embodiment, as the ultrasound probe 2, a linear scanning type electronic scanning probe is adopted. However, either the electronic scanning type or a mechanical scanning type may be adopted, or any of the linear scanning type, a sector scanning system, and a convex scanning system can be adopted.

As illustrated in FIG. 2, the ultrasound diagnostic apparatus body 1 includes, for example, an operation interface 11, a transmitter 12, a receiver 13, an image generator 14, an image processor 15 as a combiner, and a digital scan converter (DSC) 16, a display 17, a hardware processor 18 as an evaluator, a combiner, a calculator, a determinator, and a storage 19.

The operation interface 11 is, for example, a console including various switches, various keys (hard keys), a trackball, a mouse, and a keyboard for inputting a command to start diagnosis or data, such as personal information of the subject, and outputs an operation signal corresponding to an operation input from the user, such as a doctor or a technician, to the hardware processor 18.

The transmitter 12 is a circuit that supplies a driving signal, which is an electrical signal, to the ultrasound probe 2 through the cable 3 under the control of the hardware processor 18 so that the ultrasound probe 2 generates transmission ultrasound waves. The transmitter 12 includes, for example, a clock generator, a delay circuit, and a pulse generator. The clock generator is a circuit that generates a clock signal for determining the transmission timing or the transmission frequency of the driving signal. The delay circuit is a circuit that sets a delay time of the transmission timing of the driving signal for each of the individual paths corresponding to the respective transducers and delays the transmission of the driving signal by the set delay time so that focusing of the transmission beam formed by transmission ultrasound waves is performed. The pulse generator is a circuit for generating a pulse signal as a driving signal at predetermined periods. The transmitter 12 configured as described above generates ultrasound waves by driving, for example, consecutive some (for example, 64) of a plurality of (for example, 192) transducers arranged in the ultrasound probe 2. Then, the transmitter 12 performs a scan by shifting the transducers to be driven in the azimuth direction each time a transmission ultrasound wave is generated.

The receiver 13 is a circuit that receives a reception signal, which is an electrical signal, from the ultrasound probe 2 through the cable 3 under the control of the hardware processor 18. The receiver 13 includes, for example, an amplifier, an A/D conversion circuit, and a phasing addition circuit. The amplifier is a circuit for amplifying the reception signal at a preset gain for each individual path corresponding to each transducer. The A/D conversion circuit is a circuit for performing A/D conversion of the amplified reception signal. The phasing addition circuit is a circuit that adjusts the time phase by giving a delay time to each individual path corresponding to each transducer for the A/D-converted reception signal and adds up (phasing addition) the time phases to generate sound ray data.

The image generator 14 generates B-mode image data by performing envelope detection processing, log compression, and the like on the sound ray data from the receiver 13, adjusting the dynamic range or gain, and performing brightness conversion under the control of the hardware processor 18. That is, the B-mode image data indicates the strength of the reception signal with the brightness. In addition to the B-mode image data, the image generator 14 may be able to generate image data using a Doppler method.

The image processor 15 includes an image memory 15a and a panoramic image memory 15b configured by a semiconductor memory, such as a dynamic random access memory (DRAM). The image memory 15a stores the B-mode image data output from the image generator 14 in units of frames. Under the control of the hardware processor 18, the image processor 15 stores the B-mode image data output from the image generator 14 in the image memory 15a in units of frames, and appropriately performs image processing on the B-mode image data for each frame. The image data in units of frames may be referred to as ultrasound image data or frame image data.

As one of the image processing, the image processor 15 has a function of generating panoramic image data with a wide field of view by continuously combining B-mode image data of a plurality of frames whose positions are adjacent to each other when the ultrasound probe 2 is moved in the opening direction (azimuth direction, scanning direction). For example, the image processor 15 performs combination into panoramic image data using Helmert transformation considering parallel movement, rotation, and enlargement and reduction or affine transformation considering not only the parallel movement, rotation, and enlargement and reduction but also shear deformation. The Helmert transformation is expressed by the following Equations (1) and (2).

$$\begin{pmatrix} x' \\ y' \end{pmatrix} = T \begin{pmatrix} x \\ y \\ 1 \end{pmatrix} \quad (1)$$

$$T = \begin{pmatrix} R\cos\theta & R\sin\theta & \Delta x \\ -R\sin\theta & R\cos\theta & \Delta y \end{pmatrix} \quad (2)$$

x' is a horizontal coordinate after conversion, y' is a vertical coordinate after conversion, x is a horizontal coordinate before conversion, y is a vertical coordinate before conversion, T is a conversion matrix, θ is a rotation amount, Δx is a horizontal parallel movement amount, Δy is a vertical parallel movement amount, and R is an enlargement/reduction rate.

The affine transformation is expressed by Equation (1) and the following Equation (3).

$$T = \begin{pmatrix} a & b & \Delta x \\ c & d & \Delta y \end{pmatrix} \quad (3)$$

x' is a horizontal coordinate after conversion, y' is a vertical coordinate after conversion, x is a horizontal coordinate before conversion, y is a vertical coordinate before conversion, T is a conversion matrix, and a, b, c, and d are conversion coefficients.

The panoramic image memory 15b stores the panoramic image data generated by the image processor 15. The frame image data stored in the image memory 15a and the panoramic image data stored in the panoramic image memory 15b are output to the DSC 16 under the control of the hardware processor 18.

Under the control of the hardware processor 18, the DSC 16 performs coordinate conversion or the like on the frame image data and the panoramic image data, which are received from the image processor 15, for conversion into an image signal for the display 17, and outputs the image signal to the display 17.

Display devices, such as a liquid crystal display (LCD), a cathode-ray tube (CRT) display, an organic electronic luminescence (EL) display, an inorganic EL display, and a plasma display, can be applied as the display 17. The display 17 displays an image on the display screen according to the image signal output from the DSC 16. The ultrasound diagnostic apparatus 100 may be configured to include a touch panel that is provided on the screen of the display 17 to receive a touch input from the user.

The hardware processor 18 includes, for example, a central processing unit (CPU), a read only memory (ROM), and a random access memory (RAM), reads various processing programs, such as a system program stored in the ROM, and loads the processing programs to the RAM to control the operation of each unit of the ultrasound diagnostic apparatus 100 according to the loaded program. The ROM is configured by a non-volatile memory, such as a semiconductor, and stores a system program corresponding to the ultrasound diagnostic apparatus 100 and various processing programs executable on the system program, such as a first panoramic image generation program for executing a first panoramic image generation process to be described later, and various kinds of data such as a gamma table. These programs are stored in the form of computer-readable program code, and the CPU sequentially executes operations according to the program code. The RAM forms a work area for temporarily storing various programs executed by the CPU and data relevant to these programs.

The storage 19 is configured by a large-capacity recording medium, such as a hard disk drive (HDD) and a solid state drive (SSD), and stores frame image data, panoramic image data, and the like stored in association with patient information.

For each unit provided in the ultrasound diagnostic apparatus 100, some or all of the functions of the respective functional blocks can be realized as a hardware circuit such as an integrated circuit. The integrated circuit is, for example, a large scale integration (LSI), and the LSI may be called an integrated circuit (IC), a system LSI, a super LSI, or an ultra LSI depending on the degree of integration. The method of circuit integration is not limited to LSI, and may be realized by a dedicated circuit or a general-purpose processor, or a field programmable gate array (FPGA) or a reconfigurable processor capable of reconfiguring the connection or setting of circuit cells inside the LSI may be used. Alternatively, the functions of some or all of the functional blocks may be executed by software. In this case, the software is stored in one or more storage media such as a ROM, an optical disk, a hard disk, or the like, and the software is executed by an arithmetic processor.

Figure 4A:
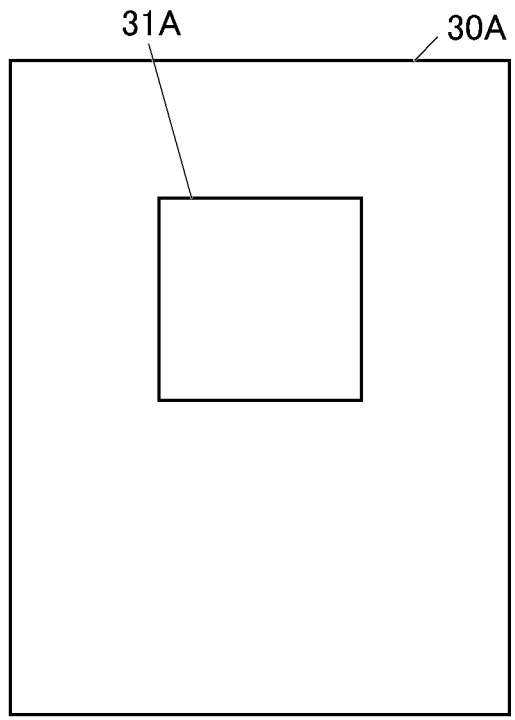
FIGS. 4A and 4B are diagrams illustrating ROIs in an ultrasound image and an ultrasound image of the next frame.
Figure 4B:
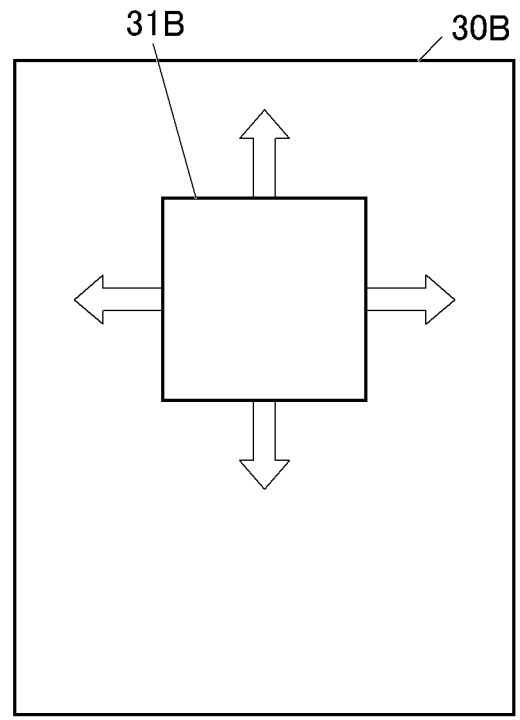
Figure 4C:
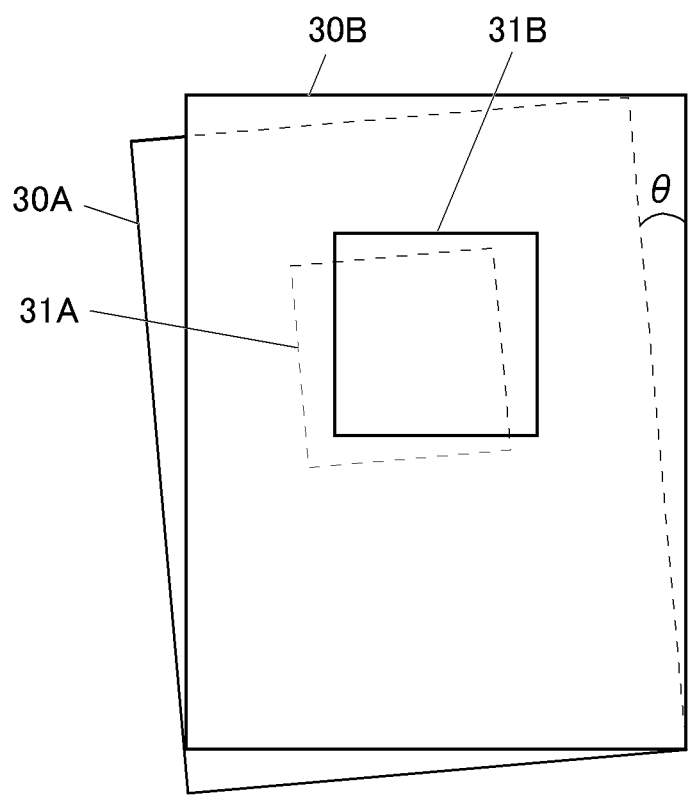
FIG. 4C is a diagram illustrating the rotation amount of the ultrasound image of the next frame with respect to the ultrasound image.

Next, the operation of the ultrasound diagnostic apparatus 100 according to the present embodiment will be described with reference to FIGS. 3 to 4C. FIG. 3 is a flowchart illustrating a first panoramic image generation process. FIGS. 4A and 4B are diagrams illustrating regions of interest (ROIs) 31A and 31B in an ultrasound image 30A and an ultrasound image 30B of the next frame. FIG. 4C is a diagram illustrating the rotation amount θ of the ultrasound image 30B of the next frame with respect to the ultrasound image 30A.

In the present embodiment, the process of generating panoramic image data using B-mode image data as tomographic image data of a plurality of frames will be described. However, the invention is not limited to this, and a process of generating panoramic image data using other pieces of tomographic image data, such as a color Doppler mode, may be performed, and the same applies to other modification examples.

It is assumed that, in the ultrasound diagnostic apparatus 100, switching to the panoramic image display mode has been made in advance by an instruction input from an operator, such as a doctor or a technician, through the operation interface 11. Then, it is assumed that the ultrasound probe 2 is applied to the subject of the patient and moved in the opening direction by the user and, under the control of the hardware processor 18, B-mode image data (ultrasound image data) of a plurality of consecutive frames for panoramic image data generation is generated and stored in the image memory 15a by the transmitter 12, the ultrasound probe 2, the receiver 13, the image generator 14 and the image processor 15, and these processes are continued until the user inputs an instruction to end the acquisition of ultrasound image data for panoramic image data generation through the operation interface 11.

Then, in the ultrasound diagnostic apparatus 100, the hardware processor 18 executes the first panoramic image generation process according to the first panoramic image generation program stored in the ROM with the ultrasound image data of a plurality of frames for panoramic image data generation being stored in the image memory 15a as a trigger.

First, the hardware processor 18 reads out and acquires ultrasound image data of temporally oldest one frame for panoramic image data generation from the image memory 15a (step S11). Then, the hardware processor 18 reads out and acquires, from the image memory 15a, the ultrasound image data of one frame acquired in step S11 or ultrasound image data of one frame temporally after ultrasound image data that has been compared (comparison source) immediately before without being deleted, and sets an ROI whose size is set in advance in the ultrasound image data of one frame acquired in step S11 or ultrasound image data before one frame that has been compared without being deleted and the acquired ultrasound image data (step S12). For example, as illustrated in FIGS. 4A and 4B, ROIs 31A and 31B are set in the ultrasound image 30A of the temporally previous ultrasound image data and the ultrasound image 30B of the ultrasound image data of the next frame, respectively. The ROIs 31A and 31B have the same shape and size. The ROI 31A in the ultrasound image 30A is set with its position fixed. The ROI 31B in the ultrasound image 30B is moved in the vertical direction and the horizontal direction. The vertical direction is a direction approximately perpendicular to the movement direction of the ultrasound probe 2 in generating panoramic image data. The horizontal direction is a movement direction of the ultrasound probe 2 in generating panoramic image data.

Then, the hardware processor 18 calculates the similarity between the brightness values in the ROIs of the two pieces of ultrasound image data set in step S12 (step S13). Then, based on the similarity between the brightness values in the ROIs calculated in step S13, the hardware processor 18 calculates the vertical movement amount, the horizontal movement amount, and the rotation amount of the ultrasound image data of the next frame acquired in step S12 with respect to the ultrasound image data as a comparison source (step S14). For example, position information of the ROI 31B in the ultrasound image 30B having a high similarity to the ROI 31A in the ultrasound image 30A illustrated in FIGS. 4A and 4B is acquired, and the movement amount in the horizontal direction and the movement amount in the vertical direction perpendicular to the contact surface of the ultrasound probe 2 with respect to the subject are calculated from the relative position information of the ROI 31B with respect to the ROI 31A. As illustrated in FIG. 4C, the ROI 31A of the ultrasound image 30A is rotated, and the rotation amount $\theta$ that increases the similarity of the ROI 31B of the ultrasound image 30B with respect to the ROI 31A is calculated.

Then, the hardware processor 18 determines whether or not the vertical movement amount as an index regarding suitability of combination for panoramic image data generation calculated in step S14 is larger than a predetermined threshold value for a vertical movement amount (step S15). That is, step S15 corresponds to the evaluation of the index, and the larger the index value is, the less suitable the combination is and the lower the evaluation result (reliability) is. Accordingly, step S15 corresponds to the determination regarding whether or not the evaluation result is lower than the threshold value. The evaluation result (reliability) shows a larger value as the suitability (reliability) of the ultrasound image data for combination for panoramic image data generation becomes larger. When the vertical movement amount is equal to or less than the threshold value (when the evaluation result is equal to or greater than the threshold value) (step S15; NO), the hardware processor 18 stores ultrasound image data of new one frame compared in the image memory 15a (step S16).

Then, the hardware processor 18 causes the image processor 15 to generate new panoramic image data by combining the panoramic image data stored in the panoramic image memory 15b (when no panoramic image data is stored, the ultrasound image data of one frame acquired in step S11) and the ultrasound image data of one frame acquired in step S12 using the vertical movement amount, the horizontal movement amount, and the rotation amount calculated in step S14, and stores the new panoramic image data in the panoramic image memory 15b (updates old panoramic image data) (step S17).

Then, the hardware processor 18 determines whether or not ultrasound image data of the next frame that has not been compared is stored in the image memory 15a (step S18). When the vertical movement amount is larger than the threshold value (when the evaluation result is lower than the threshold value) (step S15; YES), the hardware processor 18 deletes the ultrasound image data of one frame acquired in step S12 from the image memory 15a (step S19), and proceeds to step S18.

When the ultrasound image data of the next frame is stored (step S18; YES), the process proceeds to step S12. When the ultrasound image data of the next frame is not stored (step S18; NO), the first panoramic image generation process ends. After the end of the first panoramic image generation process, the panoramic image data stored in the panoramic image memory 15b is displayed on the display 17 through the DSC 16 by the hardware processor 18 and stored in the storage 19 in response to a save instruction input from the user through the operation interface 11.

As described above, according to the present embodiment, the ultrasound diagnostic apparatus 100 includes: the image generator 14 that generates ultrasound image data from the reception signal obtained from the moving ultrasound probe 2; and the hardware processor 18 that evaluates the index regarding the suitability of combining a plurality of pieces of ultrasound image data, which are generated by the image generator 14 and stored in the image memory 15a, generates an evaluation result, selects ultrasound image data according to the generated evaluation result, and causes the image processor 15 to combine the selected ultrasound image data to generate panoramic image data. The hardware processor 18 selects ultrasound image data having a high evaluation result generated.

Therefore, ultrasound image data with a high index evaluation result can be selected and used for combination, and ultrasound image data with a low index evaluation result cannot be used for combination. As a result, it is possible to obtain panoramic image data useful for diagnosis and to reduce the risk of re-acquisition of panoramic image data. Panoramic image data useful for diagnosis can be efficiently obtained.

The hardware processor 18 calculates the vertical movement amount and the movement amount in the horizontal direction, which is the movement direction of the ultrasound probe 2, in a plurality of pieces of ultrasound image data, and combines the plurality of selected pieces of ultrasound image data based on the calculated vertical movement amount and horizontal movement amount. The vertical direction is a direction approximately perpendicular to the movement direction of the ultrasound probe 2. Therefore, it is possible to improve the accuracy of combining a plurality of pieces of ultrasound image data.

The hardware processor 18 calculates the rotation amount in the plurality of pieces of ultrasound image data, and combines the plurality of selected pieces of ultrasound image data based on the calculated rotation amount. Therefore, a panoramic image of a curved subject can be captured by using the rotation amount for combination.

The index is a movement amount in the vertical direction perpendicular to the contact surface of the ultrasound probe 2 with respect to the subject in a plurality of pieces of ultrasound image data. The hardware processor 18 lowers the evaluation result when the vertical movement amount is larger than the threshold value for the vertical movement amount. Therefore, it is possible to appropriately evaluate the suitability of the combination for panoramic image data generation according to the vertical movement amount.

The hardware processor 18 deletes ultrasound image data, which has a low evaluation result generated, from the image memory 15a in which a plurality of pieces of ultrasound image data are stored. Therefore, the capacity of the image memory 15a can be saved by discarding ultrasound image data unnecessary for combination.

First Modification Example

A first modification example of the above-described embodiment will be described with reference to FIG. 5. FIG. 5 is a flowchart illustrating a second panoramic image generation process.

In the above-described embodiment, ultrasound image data suitable for combination for panoramic image data generation is selected by using the vertical movement amount as an index. In this modification example, however, ultrasound image data suitable for combination for panoramic image data generation is selected by using a movement amount ratio, which is a ratio of the vertical movement amount to the horizontal movement amount, as an index.

In this modification example, as in the embodiment described above, the ultrasound diagnostic apparatus 100 is used. However, it is assumed that, instead of the first panoramic image generation program, a second panoramic image generation program for executing a second panoramic image generation process described later is stored in the ROM of the hardware processor 18.

Next, the operation of the ultrasound diagnostic apparatus 100 of this modification example will be described with reference to FIG. 5. As in the embodiment described above, ultrasound image data of a plurality of frames of a subject for panoramic image data generation is acquired and stored in the image memory 15a until an instruction to end the acquisition of ultrasound image data is input.

In the ultrasound diagnostic apparatus 100, the hardware processor 18 executes the second panoramic image generation process according to the second panoramic image generation program stored in the ROM with the ultrasound image data of a plurality of frames for panoramic image data generation being stored in the image memory 15a as a trigger.

As illustrated in FIG. 5, steps S21 to S23 are the same as steps S11 to S13 of the first panoramic image generation process in FIG. 3. Then, based on the similarity between the brightness values in the ROI calculated in step S13, the hardware processor 18 calculates a vertical movement amount, a horizontal movement amount, a movement amount ratio that is a ratio of the vertical movement amount to the horizontal movement amount, and a rotation amount in ultrasound image data of the next frame acquired in step S12 with respect to the ultrasound image data as a comparison source (step S24).

Then, the hardware processor 18 determines whether or not the movement amount ratio as an index calculated in step S24 is larger than a predetermined threshold value for a movement amount ratio (step S25). That is, step S25 corresponds to the evaluation of the index, and the larger the index value, the lower the evaluation result (reliability). Accordingly, step S25 corresponds to the determination regarding whether or not the evaluation result is lower than the threshold value. When the movement amount ratio is equal to or less than the threshold value (when the evaluation result is equal to or greater than the threshold value) (step S25; NO), step S26 is executed. When the movement amount ratio is larger than the threshold value (when the evaluation result is lower than the threshold value) (step S25; YES), step S29 is executed. Steps S26 to S29 are the same as steps S16 to S19 of the first panoramic image generation process in FIG. 3.

As described above, according to this modification example, the index is the movement amount ratio of the movement amount in the vertical direction to the movement amount in the horizontal direction parallel to the contact surface of the ultrasound probe 2 with respect to the subject in a plurality of pieces of ultrasound image data. The hardware processor 18 lowers the evaluation result when the movement amount ratio is larger than the threshold value for the movement amount ratio. Therefore, by adding the horizontal movement amount to the vertical movement amount to obtain the movement amount ratio, it is possible to prevent the evaluation result from becoming excessively low. Not only the movement amount ratio but also the angle formed by vectors in the vertical and horizontal directions may be used as an index.

Second Modification Example

Figure 6:
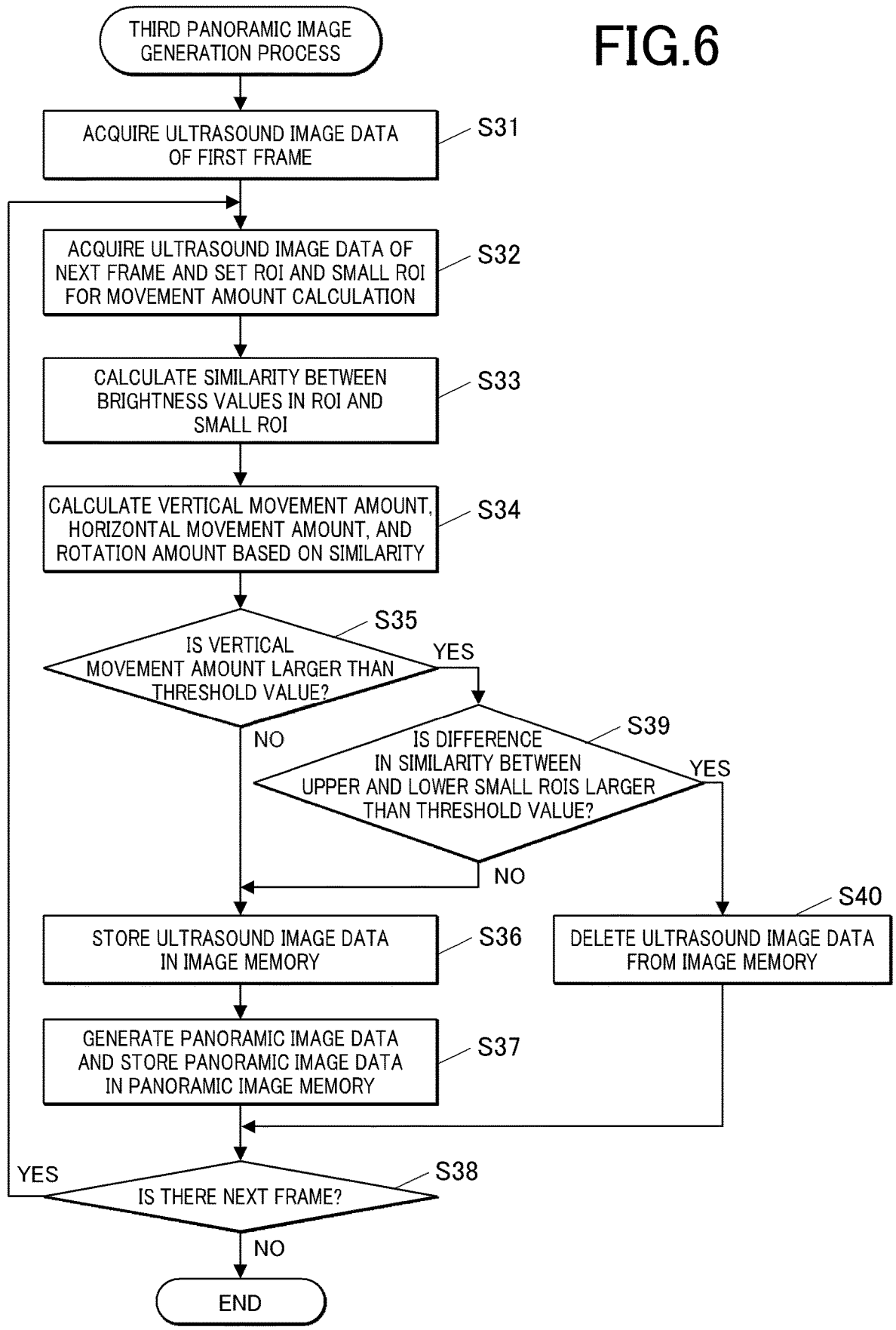
FIG. 6 is a flowchart illustrating a third panoramic image generation process.
Figure 7:
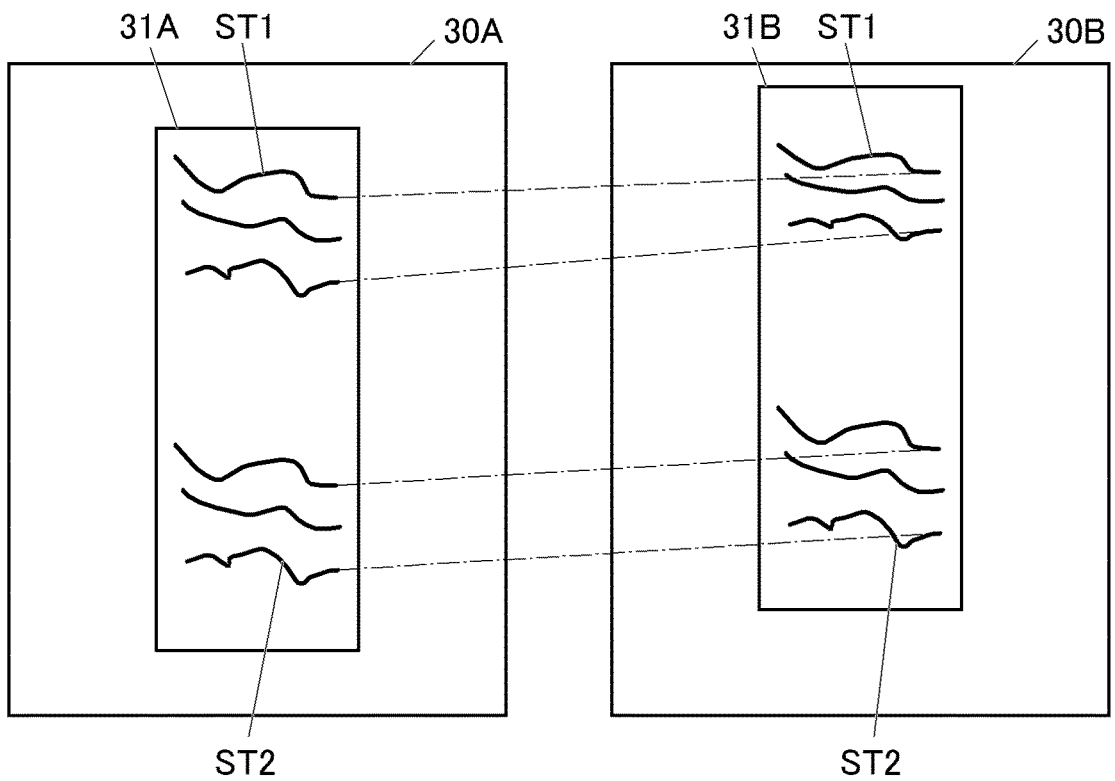
FIG. 7 is a diagram illustrating ROIs at positions having a high similarity in an ultrasound image and an ultrasound image of the next frame.
Figure 8:
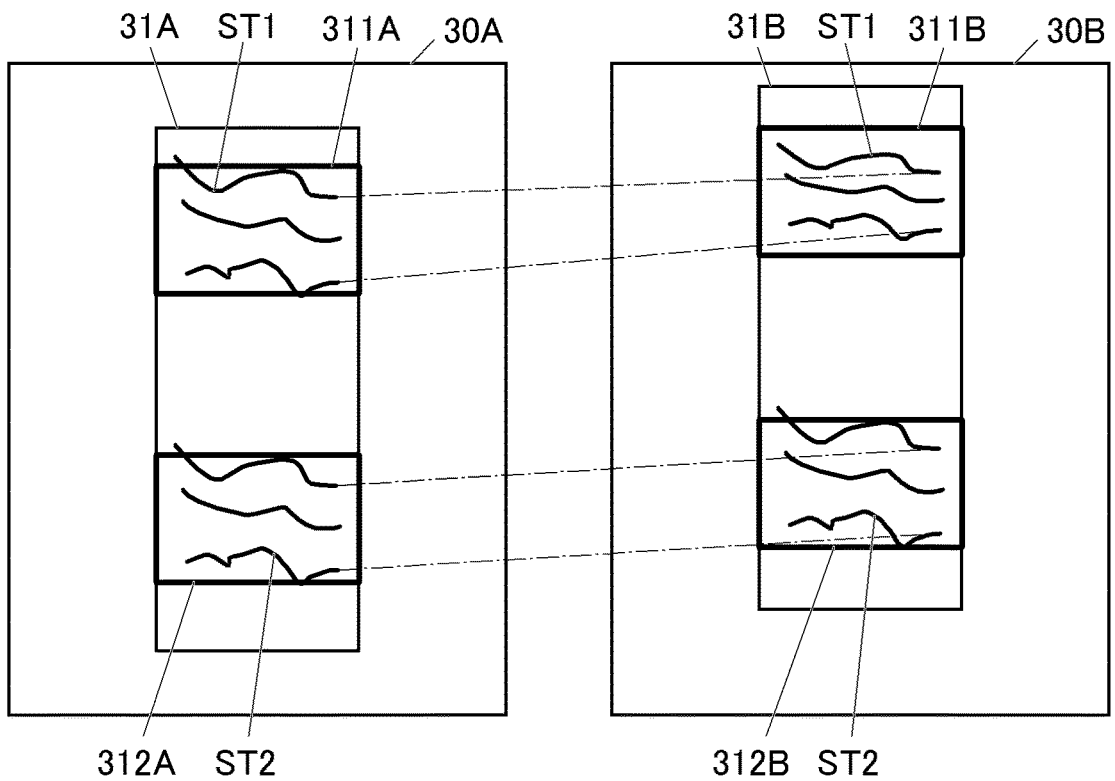
FIG. 8 is a diagram illustrating ROIs and small ROIs in an ultrasound image and an ultrasound image of the next frame.

A second modification example of the above-described embodiment will be described with reference to FIGS. 6 to 8. FIG. 6 is a flowchart illustrating a third panoramic image generation process. FIG. 7 is a diagram illustrating ROIs 31A and 31B at positions having a high similarity in the ultrasound image 30A and the ultrasound image 30B of the next frame. FIG. 8 is a diagram illustrating ROIs 31A and 31B and small ROIs 311A, 312A, 311B, and 312B in the ultrasound image 30A and the ultrasound image 30B of the next frame.

In the embodiment described above, ultrasound image data suitable for the combination for panoramic image data generation is selected using the vertical movement amount obtained using one ROI. In this modification example, however, ultrasound image data suitable for the combination for panoramic image data generation is selected using an ROI and two small ROIs in the ROI.

In this modification example, as in the embodiment described above, the ultrasound diagnostic apparatus 100 is used. However, it is assumed that, instead of the first panoramic image generation program, a third panoramic image generation program for executing a third panoramic image generation process described later is stored in the ROM of the hardware processor 18.

Next, the operation of the ultrasound diagnostic apparatus 100 of this modification example will be described with reference to FIGS. 6 to 8. As in the embodiment described above, ultrasound image data of a plurality of frames of a subject for panoramic image data generation is acquired and stored in the image memory 15a until an instruction to end the acquisition of ultrasound image data is input.

In the ultrasound diagnostic apparatus 100, the hardware processor 18 executes the third panoramic image generation process according to the third panoramic image generation program stored in the ROM with the ultrasound image data of a plurality of frames for panoramic image data generation being stored in the image memory 15a as a trigger.

As illustrated in FIG. 6, step S31 is the same as step S11 of the first panoramic image generation process in FIG. 3. Then, the hardware processor 18 acquires, from the image memory 15a, the ultrasound image data of one frame acquired in step S31 or ultrasound image data of one frame temporally after ultrasound image data that has been compared (comparison source) immediately before without being deleted, and sets an ROI having a size set in advance and two small ROIs on the upper and lower sides within the ROI in the ultrasound image data of one frame acquired in step S31 or the ultrasound image data before one frame that has been compared without being deleted and the acquired ultrasound image data (step S32).

For example, as illustrated in FIG. 7, as in the embodiment described above, it is assumed that the ROIs 31A and 31B are set in the ultrasound image 30A of the temporally previous ultrasound image data and the ultrasound image 30B of the ultrasound image data of the next frame, respectively. It is assumed that the ROIs 31A and 31B include a structure ST1 on the upper side of the subject (front surface side of the subject; the ultrasound probe 2 side) and a structure ST2 on the lower side of the subject (deep portion side of the subject). It is assumed that the ultrasound image 30B is an ultrasound image when the subject is pressed during the movement of the ultrasound probe 2. The ROI 31B is disposed at a position having a high similarity with the brightness value of the ROI 31A. Since the structure ST1 is located on the front surface side of the subject, the structure ST1 is easily distorted by pressure. Since the structure ST2 is located deeper than the structure ST1, the structure ST2 is less likely to be distorted by pressure (only parallel movement in the upward direction occurs). As described above, if there is one ROI, the upper or lower structure in the ROI is combined with the panoramic image data while being distorted.

Therefore, as illustrated in FIG. 8, small ROIs 311A (upper side) and 312A (lower side) are set in the ROI 31A of the ultrasound image 30A. The small ROIs 311A and 312A include structures ST1 and ST2, respectively. The positions of the small ROIs 311A and 312A in the ROI 31A are fixed (for example, the small ROIs 311A and 312A are disposed at positions of z1 and z2 [mm] downward from the upper side of the ROI 31A), and the positions of the small ROIs 311B and 312B in the ROI 31B are also set in the same manner. The small ROIs 311B and 312B also include the structures ST1 and ST2, respectively. The small ROIs 311A and 311B disposed on the upper sides of the ultrasound images 30A and 30B correspond to approximately the same ultrasound irradiation region.

Then, it is possible to calculate the vertical movement amount and the horizontal movement amount due to the movement of the ROI 31B with respect to the ROI 31A, and it is possible to determine whether or not the ultrasound image data of the ultrasound image 30B is suitable for the combination for panoramic image data generation according to the difference between the similarity of the small ROI 311B with respect to the small ROI 311A and the similarity of the small ROI 312B with respect to the small ROI 312A. If the difference in similarity is larger than a predetermined threshold value, for example, the similarity of the small ROI 311B with respect to the small ROI 311A may be low and accordingly the subject may be in a compressed state. For this reason, the ultrasound image 30B is not suitable for the combination for panoramic image data generation. In step S32, therefore, an ROI at a fixed position and two small ROIs on the upper and lower sides within the ROI are disposed in the ultrasound image data of the frame as a comparison source, and an ROI at a movable position and two small ROIs on the upper and lower sides within the ROI are disposed in the ultrasound image data of the next frame.

Returning to FIG. 6, the hardware processor 18 calculates the similarity between the brightness values in the ROI and the small ROIs of the two pieces of ultrasound image data set in step S32 (step S33). Then, based on the similarity between the brightness values in the ROI calculated in step S33, the hardware processor 18 calculates the vertical movement amount, the horizontal movement amount, and the rotation amount of the ultrasound image data of the next frame acquired in step S32 with respect to the ultrasound image data as a comparison source (step S34).

Steps S35, S36, S37, S38, and S40 are the same as steps S15, S16, S17, S18, and S19 of the first panoramic image generation process in FIG. 3. When the vertical movement amount is larger than the threshold value (step S35; YES), the hardware processor 18 determines whether or not the difference in similarity between the two small ROIs on the upper and lower sides within the ROI as an index calculated in step S33 is larger than a predetermined threshold value for a difference in similarity (step S39). For example, the difference in similarity is a difference between the similarity of the small ROI 311B with respect to the small ROI 311A and the similarity of the small ROI 312B with respect to the small ROI 312A in FIG. 8. That is, step S39 corresponds to the evaluation of the index, and the larger the index value, the lower the evaluation result (reliability). Accordingly, step S39 corresponds to the determination regarding whether or not the evaluation result is lower than the threshold value.

When the difference in similarity between the two upper and lower small ROIs is equal to or less than the threshold value (when the evaluation result is equal to or greater than the threshold value) (step S39; NO), the process proceeds to step S36. When the difference in similarity between the two upper and lower small ROIs is larger than the threshold value (when the evaluation result is lower than the threshold value) (step S39; YES), the process proceeds to step S40.

As described above, according to this modification example, the index is the difference in similarity between the small ROIs disposed on the upper and lower sides within the ROI set in the plurality of pieces of ultrasound image data.

The hardware processor 18 lowers the evaluation result when the difference in similarity between the small ROIs is larger than the threshold value for the difference in similarity. The small ROIs disposed on the upper sides in the plurality of pieces of ultrasound image data correspond to approximately the same ultrasound irradiation region. Therefore, by calculating the similarities between the small ROIs on the upper and lower sides, it is possible to improve the accuracy of evaluation of a plurality of pieces of ultrasound image data (it is possible to prevent the evaluation result from becoming excessively low).

Third Modification Example

Figure 10A:
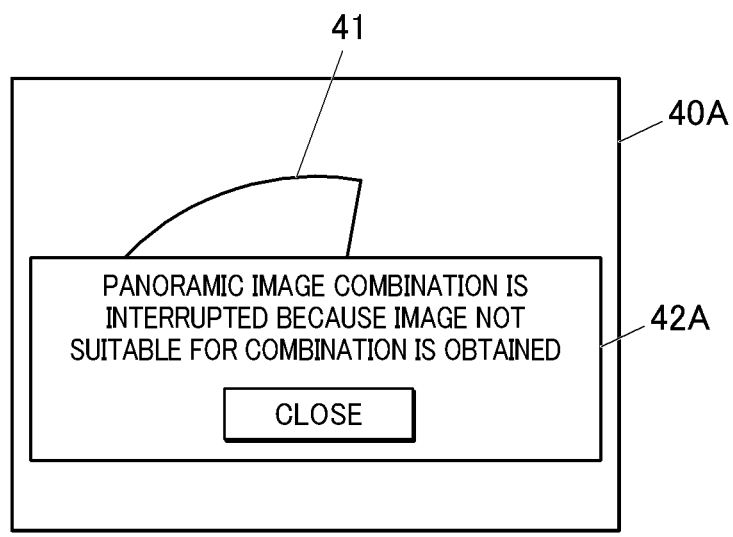
FIG. 10A is a diagram illustrating a first panoramic image display screen.
Figure 10B:
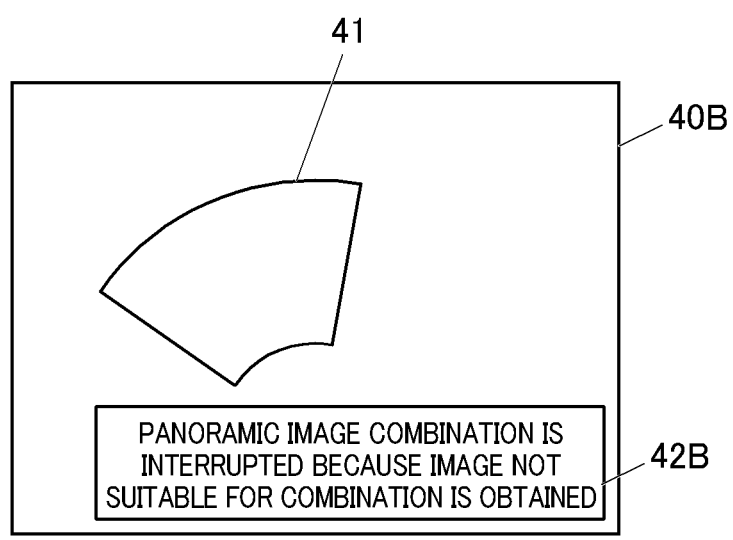
FIG. 10B is a diagram illustrating a second panoramic image display screen.

A third modification example of the above-described embodiment will be described with reference to FIGS. 9 to 10B. FIG. 9 is a flowchart illustrating a fourth panoramic image generation process. FIG. 10A is a diagram illustrating a panoramic image display screen 40A. FIG. 10B is a diagram illustrating a panoramic image display screen 40B.

In the embodiment described above, ultrasound image data is generated using ultrasound image data whose vertical movement amount as an index is equal to or less than the threshold value. In this modification example, panoramic image data generation is automatically interrupted when the evaluation result of the index of ultrasound image data is consecutively low (reliability is low).

In this modification example, as in the embodiment described above, the ultrasound diagnostic apparatus 100 is used. However, it is assumed that, instead of the first panoramic image generation program, a fourth panoramic image generation program for executing a fourth panoramic image generation process described later is stored in the ROM of the hardware processor 18.

Next, the operation of the ultrasound diagnostic apparatus 100 of this modification example will be described with reference to FIGS. 9 to 10B. As in the embodiment described above, ultrasound image data of a plurality of frames of a subject for panoramic image data generation is acquired and stored in the image memory 15a until an instruction to end the acquisition of ultrasound image data is input.

In the ultrasound diagnostic apparatus 100, the hardware processor 18 executes the fourth panoramic image generation process according to the fourth panoramic image generation program stored in the ROM with the ultrasound image data of a plurality of frames for panoramic image data generation being stored in the image memory 15a as a trigger.

As illustrated in FIG. 9, steps S51 and S52 are the same as steps S11 and S12 of the first panoramic image generation process of FIG. 3. Then, the hardware processor 18 evaluates the vertical movement amount as an index calculated in step S52 and calculates the evaluation result (step S53). For example, similar to step S15 of the first panoramic image generation process in FIG. 3, an evaluation result indicating that the higher the value is, the higher the reliability (evaluation) is, depending on whether or not the vertical movement amount is larger than the movement amount threshold value is generated.

Then, the hardware processor 18 determines whether or not the evaluation result generated in step S53 is smaller than a predetermined threshold value for an evaluation result, and determines whether or not the evaluation result is lower than the threshold value twice in a row (step S54). When the evaluation result is not consecutively lower than the threshold value (step S54; NO), the hardware processor 18 does not store the ultrasound image data of the next frame in the image memory 15a, and determines whether or not to end the acquisition of ultrasound image data (step S55). When the acquisition of ultrasound image data is not ended (step S55; NO), the process proceeds to step S52.

When the acquisition of ultrasound image data ends (step S55; YES), the hardware processor 18 causes the image processor 15 to generate panoramic image data formed by all the frames obtained by combining all the pieces of ultrasound image data stored in the image memory 15a using the vertical movement amount, the horizontal movement amount, and the rotation amount of each frame calculated in step S52, and stores the panoramic image data in the panoramic image memory 15b (step S56). Then, the hardware processor 18 displays the panoramic image data generated in step S56 on the display 17 through the DSC 16 (step S57), and ends the fourth panoramic image generation process.

When the evaluation result is consecutively lower than the threshold value (step S54; YES), the hardware processor 18 causes the image processor 15 to generate panoramic image data formed by halfway frames obtained by combining the ultrasound image data acquired in steps S11 and S12, which is stored in the image memory 15a, using the vertical movement amount, the horizontal movement amount, and the rotation amount of each frame calculated in step S52, and stores the panoramic image data in the panoramic image memory 15b (step S58). It is assumed that the ultrasound image data used for combination does not include a frame whose evaluation result is consecutively smaller than the threshold value. Then, the hardware processor 18 displays the panoramic image data generated in step S58 and an interruption message field indicating that the panoramic image data generation is not completed on the display 17 through the DSC 16 (step S59), and ends the fourth panoramic image generation process.

In step S59, for example, the panoramic image display screen 40A illustrated in FIG. 10A is displayed. The panoramic image display screen 40A has a panoramic image 41 and an interruption message field 42A. The panoramic image 41 is, for example, a panoramic image based on panoramic image data until the evaluation result is consecutively low when the linear scanning type ultrasound probe 2 is moved in a circular shape. The interruption message field 42A is superimposed on the panoramic image 41, has an interruption message and a close button, and the display can be erased by a close button click input from the user through the operation interface 11. In step S59, the panoramic image display screen 40B illustrated in FIG. 10B may be displayed. The panoramic image display screen 40B has the panoramic image 41 and an interruption message field 42B. The interruption message field 42B is not superimposed on the panoramic image 41 and has an interruption message. It is assumed that the messages in the interruption message fields 42A and 42B include the interruption of combination and the reason.

As described above, according to this modification example, when the evaluation results of a plurality of pieces of ultrasound image data are consecutively low, the hardware processor 18 interrupts the combination of the ultrasound image data whose evaluation results are consecutively low. Therefore, it is possible to generate panoramic image data by reliably combining ultrasound image data useful for diagnosis before the evaluation result is consecutively low, and it is possible to automatically prevent ultrasound image data not useful for diagnosis from being combined.

The hardware processor 18 causes the display 17 to display panoramic image data whose combination has been interrupted and an interruption message indicating the interruption of the combination. Therefore, it is possible to prevent an ultrasound image not useful for diagnosis from being presented to the user, and the user can easily visually recognize that the user has interrupted the combination and the reason through the interruption message.

Fourth Modification Example

Figure 12A:
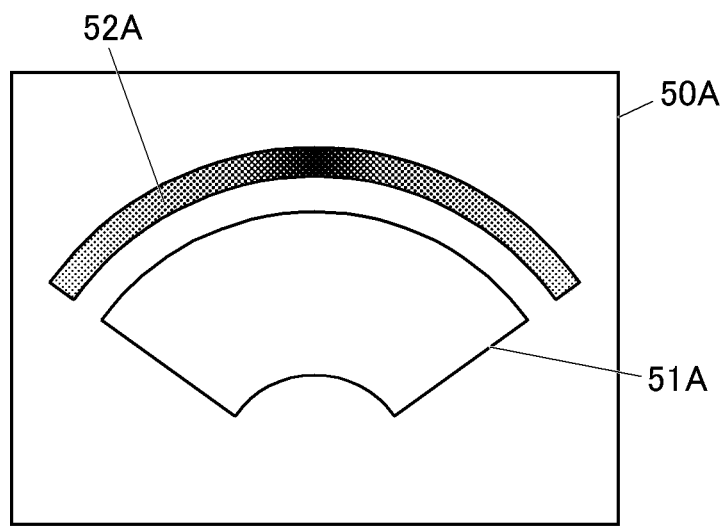
FIG. 12A is a diagram illustrating a third panoramic image display screen.
Figure 12B:
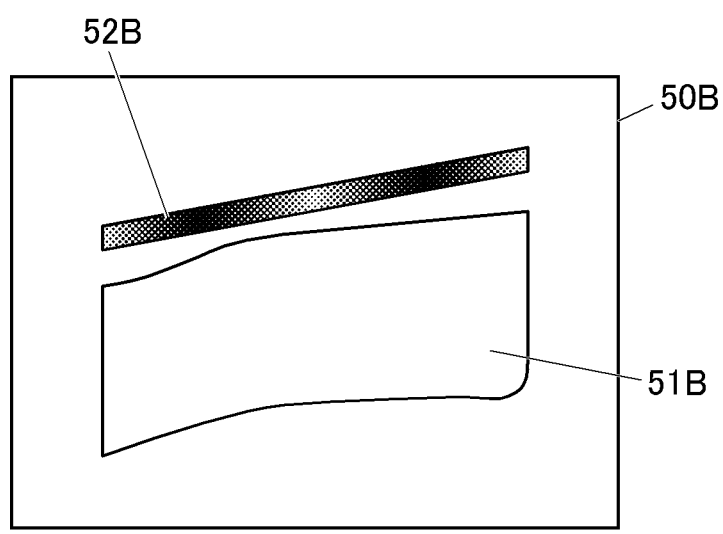
FIG. 12B is a diagram illustrating a fourth panoramic image display screen.

A fourth modification example of the above-described embodiment will be described with reference to FIGS. 11 to 12B. FIG. 11 is a flowchart illustrating a fifth panoramic image generation process. FIG. 12A is a diagram illustrating a panoramic image display screen 50A. FIG. 12B is a diagram illustrating a panoramic image display screen 50B.

In the embodiment described above, only the panoramic image data is generated and displayed. In this modification example, however, the evaluation result information of the index of the ultrasound image data is displayed together with the panoramic image data.

In this modification example, as in the embodiment described above, the ultrasound diagnostic apparatus 100 is used. However, it is assumed that, instead of the first panoramic image generation program, a fifth panoramic image generation program for executing a fifth panoramic image generation process described later is stored in the ROM of the hardware processor 18.

Next, the operation of the ultrasound diagnostic apparatus 100 of this modification example will be described with reference to FIG. 11. As in the embodiment described above, ultrasound image data of a plurality of frames of a subject for panoramic image data generation is acquired and stored in the image memory 15a until an instruction to end the acquisition of ultrasound image data is input.

In the ultrasound diagnostic apparatus 100, the hardware processor 18 executes the fifth panoramic image generation process according to the fifth panoramic image generation program stored in the ROM with the ultrasound image data of a plurality of frames for panoramic image data generation being stored in the image memory 15a as a trigger.

As illustrated in FIG. 11, steps S61 to S64 are the same as steps S51 to S54 of the third panoramic image generation process in FIG. 11. When the evaluation result is not consecutively lower than the threshold value (step S64; NO), the process proceeds to step S65. Step S65 is the same as step S55 of the third panoramic image generation process in FIG. 6. When the evaluation result is consecutively lower than the threshold value (step S64; YES), the hardware processor 18 stores ultrasound image data of a frame with a highest evaluation result generated in step S63, among a plurality of consecutive frames whose evaluation results are smaller than the threshold value, in the image memory 15a, and deletes ultrasound image data of frames other than the stored ultrasound image data, among the plurality of frames, from the image memory 15a (step S66), and the process proceeds to step S65.

When the acquisition of the ultrasound image data ends (step S65; YES), the hardware processor 18 determines a combination coefficient based on the evaluation result generated in step S63 (step S67). For example, the combination coefficient (combination weighting) is determined to become higher as the evaluation result becomes higher since the reliability becomes higher as the evaluation result becomes higher. Then, the hardware processor 18 generates panoramic image data by combining the ultrasound image data stored in the image memory 15a using the vertical movement amount, the horizontal movement amount, and the rotation amount calculated in step S62 and the combination coefficient determined in step S67, and stores the panoramic image data in the panoramic image memory 15b (step S68).

As a method of calculating (weighting method) the pixel value of the panoramic image data in step S68, the following Equations (4) and (5) are used. When image data as a combination source includes panoramic image data (image data that has already been combined), the pixel value of the panoramic image data is obtained by Equation (4).

$$O(x', y') = \frac{\alpha}{\alpha+\beta}I(x', y') + \frac{\beta}{\alpha+\beta}I'(x', y') \quad (4)$$

O is a pixel value after combination, I is a pixel value of an image as a combination source, I' is a pixel value of an image to be combined, $\alpha$ is the reliability (evaluation result) of an image as a combination source, and $\beta$ is the reliability of an image to be combined.

When there is no panoramic image data in the image data as a combination source, the pixel value of the panoramic image data is obtained by Equation (5).

$$O(x',y')=I'(x',y') \quad (5)$$

Then, the hardware processor 18 displays the panoramic image data generated in step S68 and the evaluation result information, which indicates the evaluation result (reliability) of panoramic image data generation, on the display 17 through the DSC 16 (step S69), and ends the fifth panoramic image generation process.

In step S69, for example, the panoramic image display screen 50A illustrated in FIG. 12A is displayed. The panoramic image display screen 50A has a panoramic image 51A and an evaluation result bar 52A as evaluation result information. The panoramic image 51A is, for example, a panoramic image based on panoramic image data when the linear scanning type ultrasound probe 2 is moved in a circular shape. The evaluation result bar 52A is disposed along a predetermined depth of the panoramic image 51A, and is a bar for multi-step gray display of the value of the evaluation result (reliability), which corresponds to each position in the horizontal direction of the panoramic image 51A (movement direction of the ultrasound probe 2), between white (highest reliability) and black (lowest reliability). The panoramic image display screen 50B illustrated in FIG. 12B may be displayed. The panoramic image display screen 50B has a panoramic image 51B and an evaluation result bar 52B. The panoramic image 51A is, for example, a panoramic image based on panoramic image data when the linear scanning type ultrasound probe 2 is moved approximately parallel to the subject. The evaluation result bar 52B is a bar for gray display of the value of the evaluation result (reliability) corresponding to each position in the horizontal direction of the panoramic image 51B (movement direction of the ultrasound probe 2). However, the evaluation result bars 52A and 52B are not limited to the gray display as a grayscale display of black and white, and may be expressed by other display methods, such as grayscale display of other colors or color mapping.

As described above, according to this modification example, when the evaluation results of a plurality of pieces of ultrasound image data are consecutively low, the hardware processor 18 selects ultrasound image data having the highest evaluation result among the plurality of pieces of ultrasound image data whose evaluation results are consecutively low. Therefore, by using ultrasound image data having the highest evaluation result as much as possible, ultrasound image data useful for diagnosis can be combined to generate panoramic image data.

The hardware processor 18 determines a combination coefficient based on the evaluation result, and combines the plurality of selected pieces of ultrasound image data based on the determined combination coefficient. Therefore, it is possible to prevent the user's operation from being interrupted by avoiding the automatic combination interruption, and the risk of generating panoramic image data including a large amount of ultrasound image data that is not useful for diagnosis can be reduced by combination using a combination coefficient.

The hardware processor 18 also causes the display 17 to display the generated panoramic image data and an evaluation result bar indicating the evaluation result of the panoramic image data. Therefore, it is possible to make it easy for the user to visually recognize a portion, which may not be useful for diagnosis, in the panoramic image.

The descriptions in the embodiment and the modification examples described above are examples of the preferred ultrasound diagnostic apparatus, panoramic image generation method, and program according to the present invention, and the present invention is not limited to these. At least two of the embodiment and the modification examples described above may be combined appropriately.

The detailed configuration and detailed operation of each unit configuring the ultrasound diagnostic apparatus 100 in the embodiment and the modification examples described above can be appropriately changed without departing from the spirit of the present invention.

Although embodiments of the present invention have been described and illustrated in detail, the disclosed embodiments are made for purposes of illustration and example only and not limitation. The scope of the present invention should be interpreted by terms of the appended claims

What is claimed is:

1. An ultrasound diagnostic apparatus, comprising:
an image generator that generates ultrasound image data based on a reception signal obtained from a moving ultrasound probe;
an evaluator that evaluates an index regarding suitability of combining a plurality of pieces of ultrasound image data generated by the image generator and generates an evaluation result; and
a combiner that selects ultrasound image data according to the generated evaluation result and combines the ultrasound image data to generate panoramic image data,
wherein:
the index is a movement amount in a vertical direction perpendicular to a contact surface of the ultrasound probe with respect to a subject in the plurality of pieces of ultrasound image data and the evaluator lowers the evaluation result when the vertical movement amount is larger than a first threshold value, or
the index is a movement amount ratio of a movement amount in a vertical direction to a movement amount in a horizontal direction parallel to a contact surface of the ultrasound probe with respect to the subject in the plurality of pieces of ultrasound image data and the evaluator lowers the evaluation result when the movement amount ratio is larger than a second threshold value.

2. The ultrasound diagnostic apparatus according to claim 1,
wherein the combiner selects ultrasound image data for which the generated evaluation result is higher than a threshold value.

3. The ultrasound diagnostic apparatus according to claim 1, further comprising:
a calculator that calculates the movement amount in the vertical direction and the movement amount in the horizontal direction, which is a movement direction of the ultrasound probe, in the plurality of pieces of ultrasound image data,
wherein the combiner combines the plurality of selected pieces of ultrasound image data based on the vertical movement amount and the horizontal movement amount.

4. The ultrasound diagnostic apparatus according to claim 3,
wherein the vertical direction is a direction approximately perpendicular to the movement direction of the ultrasound probe.

5. The ultrasound diagnostic apparatus according to claim 3,
wherein the calculator calculates a rotation amount in the plurality of pieces of ultrasound image data, and
the combiner combines the plurality of selected pieces of ultrasound image data based on the calculated rotation amount.

6. The ultrasound diagnostic apparatus according to claim 1,
wherein the index is the movement amount in the vertical direction perpendicular to the contact surface of the ultrasound probe with respect to the subject in the plurality of pieces of ultrasound image data, and
the evaluator lowers the evaluation result when the vertical movement amount is larger than the first threshold value.

7. The ultrasound diagnostic apparatus according to claim 1,
wherein the index is the movement amount ratio of the movement amount in the vertical direction to the movement amount in the horizontal direction parallel to the contact surface of the ultrasound probe with respect to the subject in the plurality of pieces of ultrasound image data, and
the evaluator lowers the evaluation result when the movement amount ratio is larger than the second threshold value.

8. The ultrasound diagnostic apparatus according to claim 1,
wherein the index further includes a difference in a similarity between an upper small region of interest of a first frame of ultrasound image data and an upper small region of interest of a second frame of ultrasound image data and a similarity between a lower small region of interest of the first frame of ultrasound image data and a lower small region of interest of the second frame of ultrasound image data, and
the evaluator lowers the evaluation result when the difference is larger than a third threshold value.

9. The ultrasound diagnostic apparatus according to claim 8,
wherein the small regions of interest disposed on the upper sides in the plurality of pieces of ultrasound image data correspond to a same ultrasound irradiation region of a subject.

10. The ultrasound diagnostic apparatus according to claim 1,
wherein the combiner deletes ultrasound image data, for which the generated evaluation result is lower than a threshold value, from a storage that stores the plurality of pieces of ultrasound image data.

11. The ultrasound diagnostic apparatus according to claim 1,
wherein, when evaluation results of the plurality of pieces of ultrasound image data are consecutively lower than a threshold value, the combiner interrupts combination of a plurality of pieces of ultrasound image data for which the evaluation results are consecutively lower than the threshold value.

12. The ultrasound diagnostic apparatus according to claim 11,
wherein the combiner causes a display to display panoramic image data for which the combination has been interrupted, and interruption information indicating interruption of the combination.

13. The ultrasound diagnostic apparatus according to claim 1,
wherein, when evaluation results of the plurality of pieces of ultrasound image data are consecutively lower than a threshold value, the combiner selects ultrasound image data having a highest evaluation result among a plurality of pieces of ultrasound image data for which the evaluation results are consecutively lower than a threshold value.

14. The ultrasound diagnostic apparatus according to claim 1, further comprising:
a determiner that determines a combination coefficient based on the evaluation result,
wherein the combiner combines the plurality of selected pieces of ultrasound image data based on the determined combination coefficient.

15. The ultrasound diagnostic apparatus according to claim 14,
wherein the combiner causes the display to display the generated panoramic image data and evaluation result information indicating an evaluation result of the panoramic image data.

16. A panoramic image generation method, comprising:
generating ultrasound image data based on a reception signal obtained from a moving ultrasound probe;
evaluating an index regarding suitability of combining a plurality of pieces of ultrasound image data generated in the generating of the ultrasound image data and generating an evaluation result; and
selecting ultrasound image data according to the generated evaluation result and combining the ultrasound image data to generate panoramic image data,
wherein:
the index is a movement amount in a vertical direction perpendicular to a contact surface of the ultrasound probe with respect to a subject in the plurality of pieces of ultrasound image data and the evaluator lowers the evaluation result when the vertical movement amount is larger than a first threshold value, or
the index is a movement amount ratio of a movement amount in a vertical direction to a movement amount in a horizontal direction parallel to a contact surface of the ultrasound probe with respect to the subject in the plurality of pieces of ultrasound image data and the evaluator lowers the evaluation result when the movement amount ratio is larger than a second threshold value.

17. A non-transitory recording medium storing a computer readable program causing a computer to perform:
generating ultrasound image data based on a reception signal obtained from a moving ultrasound probe;
evaluating an index regarding suitability of combining a plurality of pieces of ultrasound image data generated in the generating of the ultrasound image data and generating an evaluation result; and
selecting ultrasound image data according to the generated evaluation result and combining the ultrasound image data to generate panoramic image data,
wherein:
the index is a movement amount in a vertical direction perpendicular to a contact surface of the ultrasound probe with respect to a subject in the plurality of pieces of ultrasound image data and the evaluator lowers the evaluation result when the vertical movement amount is larger than a first threshold value, or
the index is a movement amount ratio of a movement amount in a vertical direction to a movement amount in a horizontal direction parallel to a contact surface of the ultrasound probe with respect to the subject in the plurality of pieces of ultrasound image data and the evaluator lowers the evaluation result when the movement amount ratio is larger than a second threshold value will.

* * * * *